United States Patent
Warner et al.

(10) Patent No.: US 10,442,823 B2
(45) Date of Patent: Oct. 15, 2019

(54) FUNCTIONALIZED F-POSS MONOMER COMPOSITIONS AND USES THEREOF

(71) Applicant: NBD NANOTECHNOLOGIES, INC, Danvers, MA (US)

(72) Inventors: John C. Warner, Wilmington, MA (US); Jean R. Loebelenz, Essex, MA (US); Srinivasa Rao Cheruku, Lexington, MA (US); Thomas Woodrow Gero, Stow, MA (US); Perry L. Catchings, Sr., Roxbury, MA (US)

(73) Assignee: NBD NANOTECHNOLOGIES, INC., Danvers, MA (US)

( * ) Notice: Subject to any disclaimer, the term of this patent is extended or adjusted under 35 U.S.C. 154(b) by 0 days.

(21) Appl. No.: 15/705,089

(22) Filed: Sep. 14, 2017

(65) Prior Publication Data
US 2018/0094006 A1 Apr. 5, 2018

Related U.S. Application Data

(63) Continuation-in-part of application No. 15/065,289, filed on Mar. 9, 2016, and a continuation-in-part of application No. 15/230,697, filed on Aug. 8, 2016, which is a continuation of application No. 14/876,911, filed on Oct. 7, 2015, now Pat. No. 9,409,933.

(60) Provisional application No. 62/130,170, filed on Mar. 9, 2015, provisional application No. 62/060,622, filed on Oct. 7, 2014.

(51) Int. Cl.
| | |
|---|---|
| *C07F 7/21* | (2006.01) |
| *C09D 7/62* | (2018.01) |
| *C08G 77/24* | (2006.01) |
| *C08G 77/04* | (2006.01) |
| *C08L 83/04* | (2006.01) |
| *C08K 5/549* | (2006.01) |
| *C09D 183/08* | (2006.01) |

(52) U.S. Cl.
CPC ............. *C07F 7/21* (2013.01); *C08G 77/045* (2013.01); *C08G 77/24* (2013.01); *C08K 5/549* (2013.01); *C08L 83/04* (2013.01); *C09D 7/62* (2018.01); *C09D 183/08* (2013.01)

(58) Field of Classification Search
None
See application file for complete search history.

(56) References Cited

U.S. PATENT DOCUMENTS

| | | | |
|---|---|---|---|
| 6,716,919 B2 | 4/2004 | Lichtenhan et al. | |
| 7,129,370 B2 | 10/2006 | Yamahiro et al. | |
| 7,193,015 B1 | 3/2007 | Mabry et al. | |
| 7,662,985 B2 | 2/2010 | Yamahiro et al. | |
| 7,863,396 B2 | 1/2011 | Yamahiro et al. | |
| 7,964,692 B2 | 6/2011 | Yamahiro et al. | |
| 9,409,933 B2 | 8/2016 | Warner | |
| 2004/0180288 A1 | 9/2004 | Adegawa | |
| 2005/0033077 A1 | 2/2005 | Yamahiro et al. | |
| 2005/0215807 A1 | 9/2005 | Morimoto et al. | |
| 2005/0250925 A1 | 11/2005 | Oikawa et al. | |
| 2006/0175684 A1 | 8/2006 | Oikawa et al. | |
| 2006/0287454 A1 | 12/2006 | Yamahiro et al. | |
| 2008/0221262 A1 | 9/2008 | Mabry et al. | |
| 2010/0035070 A1 | 2/2010 | Moorlag et al. | |
| 2010/0222503 A1 | 9/2010 | Laine et al. | |
| 2012/0205315 A1 | 8/2012 | Liu et al. | |
| 2013/0072609 A1 | 3/2013 | Haddad et al. | |
| 2014/0046005 A1 | 2/2014 | Leong et al. | |
| 2014/0238263 A1 | 8/2014 | Scheonfisch et al. | |
| 2014/0275598 A1 | 9/2014 | Freeman et al. | |
| 2014/0323005 A1 | 10/2014 | Dooley et al. | |
| 2016/0096853 A1 | 4/2016 | Warner | |

FOREIGN PATENT DOCUMENTS

| | | | |
|---|---|---|---|
| CN | 1100838 C | 2/2003 | |
| CN | 101762835 A | 6/2010 | |
| JP | 2005272506 A | 10/2005 | |
| JP | 2006096735 A | 4/2006 | |
| JP | 2012251035 A | 12/2012 | |
| WO | WO-0110871 A1 * | 2/2001 | ............ C07F 7/0874 |
| WO | 2016134207 A1 | 8/2016 | |
| WO | 2016145060 A1 | 9/2016 | |

OTHER PUBLICATIONS

Wang et al.; POSS-based luminescent porous polymers for carbon dioxide sorption and nitroaromatic explosives detection; RSC Advances; Oct. 27, 2014; vol. 4, pp. 59877-59884.
Search Report for European Patent Application No. 16762413.9; dated Sep. 25, 2018.
STN search results; U.S. Appl. No. 15/065,289, filed Apr. 17, 2018.
Chhatre et al.; Fluoroalkylated Silicon-Containing Surfaces—Estimation of Solid-Surface Energy; ACS Appl. Mater. Interfaces; 2010; vol. 2; pp. 3544-3554.
Kota et al.; The design and applications of superomniphobic surfaces; NPG Asia Materials; 2014; vol. 6.
Mabry et al.; Fluorinated Polyhedral Oligomeric Silsesquioxanes (F-Poss); Angew. Chem.; Int. Ed. 2008; vol. 47, Issue 22; pp. 4137-4140.
Mabry; Nanostructured Materials, in-House Report, Air Force Research Laboratory, Aug. 2012, pp. 1-63.

(Continued)

*Primary Examiner* — Clinton A Brooks
*Assistant Examiner* — Kofi Adzamli
(74) *Attorney, Agent, or Firm* — Barnes & Thornburg LLP; Jason Bernstein

(57) ABSTRACT

Functionalized F-POSS compounds comprising synthetic blends of at least two feedstocks that produce a distribution of fluorinated polyhedral oligomeric silsesquioxane molecule structures and/or functional groups.

20 Claims, 4 Drawing Sheets

(56) References Cited

OTHER PUBLICATIONS

Taylor et al.: Further studies of fluoride ion entrapment in octasilsesquioxane cases; X-ray crystal structure studies and factors that affect their formation; Dalton Trans.; 2012; vol. 41, pp. 2048-2059.
Tuteja et al.; Designing Superoleophobic Surfaces; Science; 2007; vol. 318; pp. 1618-1622.
Tuteja et al.; Robust omniphobic surfaces; Proc. Natl. Acad. Sci. U.S.A.; 2008; vol. 105; pp. S18200/1-S18200/29.
Search Report and Written Opinion for International Patent Application No. PCT/US2016/021532; dated Jun. 3, 2016.
International Preliminary Report on Patentability for International Patent Application No. PCT/US2015/054367; dated Apr. 20, 2017.
Koh et al.; Precision Synthesis of a Fluorinated Polyhedral Oligomeric Silsesquioxane-Terminated Polymer and Surface Characterization of Its Blend Film with Poly(methyl methacrylate); Macromolecules; 2005; pp. 1264-1270; vol. 38.
Extended European Search Report for European Patent Application No. 18194643.5; dated Jan. 21, 2019.

\* cited by examiner

FUNCTIONALIZED F-POSS MONOMER COMPOSITIONS AND USES THEREOF

CROSS-REFERENCE TO RELATED APPLICATION

This application is a continuation-in-part of U.S. patent application Ser. No. 15/065,289, filed on Mar. 9, 2016, which claims benefit of U.S. Provisional Patent Application No. 62/130,170, filed on Mar. 9, 2015, and is a continuation-in-part of U.S. patent application Ser. No. 15/230,697, filed on Aug. 8, 2016, which is a continuation of U.S. patent application Ser. No. 14/876,911, filed on Oct. 7, 2015, which claims benefit of U.S. Provisional Patent Application No. 62/060,622, filed on Oct. 7, 2014, and commonly assigned to the assignee of the present application, the disclosures of which are incorporated by reference in their entirety herein.

FIELD

The present disclosure relates, in exemplary embodiments, to functionalized F-POSS compounds comprising synthetic blends of at least two feedstocks that produce a distribution of fluorinated polyhedral oligomeric silsesquioxane molecule structures and/or functional groups. The present disclosure also relates, in exemplary embodiments, to methods of making such compounds, and uses thereof.

BACKGROUND

Fluorinated polyhedral oligomeric silsesquioxane ("F-POSS") molecules are a subclass of polyhedral oligomeric silsesquioxanes ("POSS") which consists of a silicon-oxide core [$SiO_{1.5}$] with a periphery of long-chain fluorinated alkyl groups. F-POSS molecules possesses one of the lowest known surface energies leading to the creation of superhydrophobic and oleophobic surfaces. A feature of F-POSS material is that it ordinarily forms a siloxy cage that acts like an inorganic glass-like material, but have organic R group substituents at the matrix apices, which provides unusual properties and applications. See Formula I below.

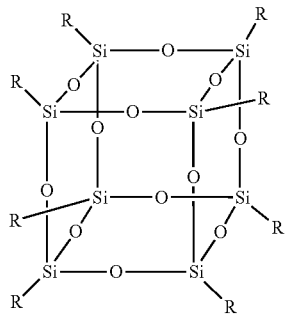

F-POSS molecules find application in material science. For example, superhydrophobic and superoleophobic surfaces have been produced using F-POSS, either cast on a substrate or blended into a polymer matrix. See, for example, Chhatre, S. S.; Guardado, J. O.; Moore, B. M.; Haddad, T. S.; Mabry, J. M.; McKinley, G. H.; Cohen, R. E. *ACS Appl. Mater. Interfaces* 2010, 2, 3544-3554; Mabry, J. M.; Vij, A.; Iacono, S. T.; Viers, B. D. *Angew. Chem., Int. Ed.* 2008, 47, 4137-4140; Tuteja, A.; Choi, W.; Mabry, J. M.; McKinely, G. H.; Cohen, R. E. *Proc. Natl. Acad. Sci. U.S.A.* 2008, 105, S18200/1-S18200/29; and Tuteja, A.; Choi, W.; Ma, M.; Mabry, J. M.; Mazzella, S. A.; Rutledge, G. C.; McKinley, G. H.; Cohen, R. E. *Science* 2007, 318, 1618-1622.

It would be desirable to provide novel functionalized F-POSS compounds for use in materials.

SUMMARY

In exemplary embodiments, a compound of the formula is provided:

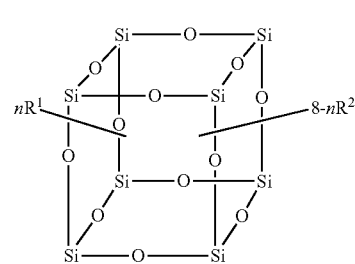

wherein $R^1$ is a long chain fluorinated alkyl; $R^2$ is selected from the group consisting of $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic and 5-7 membered heteroaryl, wherein each hydrogen atom in $R^1$ is independently optionally substituted by an $R^3$; each $R^3$ is independently selected from the group consisting of halo (i.e., any haloalkane, or alkane containing at least one atom of a halogen), $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —OR$^4$, —NR$^4$R$^5$, —OC(O)R$^4$, —C(O)OR$^4$, —C(O)R$^4$, —OC(O)OR$^4$, —C(O)NR$^4$R$^5$, —OC(O)NR$^4$R$^5$, —NR$^4$C(O)R$^5$, —NR$^4$C(O)OR$^5$ and —NR$^4$C(O)NR$^4$R$^5$, and when $R^3$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic or 5-7 membered heteroaryl, each hydrogen atom in $R^3$ is independently optionally substituted by an $R^6$; each $R^4$ and $R^5$ is independently selected from the group consisting of hydrogen, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, and 5-7 membered heteroaryl, wherein each hydrogen atom in $R^4$ and $R^5$ is independently optionally substituted by an $R^6$; each $R^6$ is independently selected from the group consisting of halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —OR$^7$, —NR$^7$R$^8$, —OC(O)R$^7$, —C(O)OR$^7$, —C(O)R$^7$, —OC(O)OR$^7$, —C(O)NR$^7$R$^8$, —OC(O)NR$^7$R$^8$, —NR$^7$C(O)R$^8$, —NR$^7$C(O)OR$^8$ and —NR$^7$C(O)NR$^7$R$^8$, and when $R^6$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic or 5-7 membered heteroaryl, each hydrogen atom in $R^6$ is independently optionally substituted by an $R^9$; each $R^7$ and $R^8$ is independently selected from the group consisting of hydrogen, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic and 5-7 membered heteroaryl, wherein each hydrogen atom in $R^7$ and $R^8$ is independently optionally substituted by one or more $R^9$; each $R^9$ is independently selected from the group consisting of hydrogen, halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —OR$^{10}$, —NR$^{10}$R$^{11}$, —OC(O)R$^{10}$, —C(O)OR$^{10}$, —C(O)R$^{10}$, —OC(O)OR$^{10}$, —C(O)NR$^{10}$R$^{11}$, —OC(O)NR$^{10}$R$^{11}$, —NR$^{10}$C(O)R$^{11}$, —NR$^{10}$C(O)OR$^{11}$ and —NR$^{10}$C(O)NR$^{10}$R$^{11}$, and when R$^9$ is C$_1$-C$_8$ alkyl, C$_2$-C$_8$ alkenyl, C$_2$-C$_8$ alkynyl, C$_6$-C$_{10}$ aryl, C$_3$-C$_8$ cycloalkyl, 5-7 membered heterocyclic, C$_3$-C$_8$ cycloalkyl or 5-7 membered heteroaryl, each hydrogen in R$^9$ is independently optionally substituted by a moiety selected from the group consisting of halo, —NCO, —OR$^{10}$, —NR$^{10}$R$^{11}$, —OC(O)R$^{10}$, —C(O)OR$^{10}$, —C(O)R$^{10}$, —OC(O)OR$^{10}$, —C(O)NR$^{10}$R$^{11}$, —OC(O)NR$^{10}$R$^{11}$, —NR$^{10}$C(O)R$^{11}$, —NR and NR each R$^{10}$ and R$^{11}$ is independently selected from the group consisting of H, C$_1$-C$_8$ alkyl, C$_2$-C$_8$ alkenyl and C$_2$-C$_8$ alkynyl, and when R$^{10}$ or R$^{11}$ are C$_1$-C$_8$ alkyl, C$_2$-C$_8$ alkenyl or C$_2$-C$_8$ alkynyl, each hydrogen atom in R$^{10}$ and R$^{11}$ is independently optionally substituted by a fluorine atom; n is an integer from 0 to 8; and each of R$^1$ and R$^2$ is independently covalently attached at a silicon atom.

In some aspects of these embodiments, R$^2$ is C$_1$-C$_8$ alkyl, wherein each hydrogen atom in R$^2$ is independently optionally substituted by an R$^3$. In other aspects of these embodiments, R$^3$ is —NCO, —OR$^4$, —OC(O)R$^4$, —C(O)OR$^4$, —C(O)R$^4$ or —OC(O)OR$^4$. In other aspects of these embodiments, R$^4$ is C$_1$-C$_8$ alkyl, wherein each hydrogen atom in R$^4$ is independently optionally substituted by an R$^6$. In other aspects of these embodiments, R$^4$ is C$_2$-C$_8$ alkenyl, wherein each hydrogen atom in R$^4$ is independently optionally substituted by an R$^6$. In other aspects of these embodiments, R$^6$ is C$_1$-C$_8$ alkyl, —NCO, —OR$^7$, —NR$^7$R$^8$, —OC(O)R$^7$, —C(O)OR$^7$, —C(O)R$^7$ or —OC(O)OR$^7$. In other aspects of these embodiments, R$^7$ is C$_1$-C$_8$ alkyl, C$_2$-C$_8$ alkenyl, C$_2$-C$_8$ alkynyl, C$_6$-C$_{10}$ aryl or 5-7 membered heteroaryl, wherein each hydrogen atom in R$^7$ is independently optionally substituted by one or more R$^9$. In other aspects of these embodiments, R$^9$ is hydrogen or C$_1$-C$_8$ alkyl, and when R$^9$ is C$_1$-C$_8$ alkyl, R$^9$ is optionally substituted by a —OC(O)R$^{10}$. In other aspects of these embodiments, R$^{10}$ is H or C$_1$-C$_8$ alkyl, and when R$^{10}$ is C$_1$-C$_8$ alkyl, each hydrogen atom in R$^{10}$ is independently optionally substituted by a fluorine atom.

In other aspects of these embodiments, R$^2$ is n-propyl, wherein each hydrogen atom in R$^2$ is independently optionally substituted by an R$^3$. In other aspects of these embodiments, R$^3$ is —OC(O)R$^4$ or —OC(O)OR$^4$. In other aspects of these embodiments, R$^4$ is n-propyl, optionally substituted by an R$^6$. In other aspects of these embodiments, R$^4$ is —CH═CH$_2$, wherein each hydrogen atom in R$^4$ is independently optionally substituted by an R$^6$. In other aspects of these embodiments, R$^6$ is C$_1$-C$_8$ alkyl. In other aspects of these embodiments, R$^6$ is methyl.

In other aspects of these embodiments, R$^6$ is —OC(O)R$^7$ or —C(O)OR$^7$. In other aspects of these embodiments, R$^7$ is —CH═CH$_2$, optionally substituted by an R$^9$. In other aspects of these embodiments, R$^9$ is C$_1$-C$_8$ alkyl. In other aspects of these embodiments, R$^9$ is methyl.

In other embodiments, R$^2$ is C$_6$-C$_{10}$ aryl, wherein each hydrogen atom in R$^2$ is independently optionally substituted by an R$^3$. In some aspects of these embodiments, R$^3$ is C$_1$-C$_8$ alkyl, C$_2$-C$_8$ alkenyl or NCO, and when R$^3$ is C$_1$-C$_8$ alkyl or C$_2$-C$_8$ alkenyl, each hydrogen atom in R$^3$ is independently optionally substituted by an R$^6$. In other aspects of these embodiments, R$^3$ is C$_2$-C$_8$ alkenyl, wherein each hydrogen atom in R$^3$ is independently optionally substituted by an R$^6$.

In other aspects of these embodiments, R$^3$ is —CH═CH$_2$, wherein each hydrogen atom in R$^3$ is independently optionally substituted by an R$^6$. In other aspects of these embodiments, R$^6$ is methyl. In other aspects of these embodiments, R$^3$ is C$_1$-C$_8$ alkyl, wherein each hydrogen atom in R$^3$ is independently optionally substituted by an R$^6$. In other aspects of these embodiments, R$^6$ is C$_6$-C$_{10}$ aryl, wherein each hydrogen atom in R$^6$ is independently optionally substituted by an R$^9$. In other aspects of these embodiments, R$^9$ is C$_2$-C$_8$ alkenyl or NCO, and when R$^9$ is C$_2$-C$_8$ alkenyl, each hydrogen atom in R$^9$ is independently optionally substituted by a moiety selected from the group consisting of halo, —NCO, —OR$^{10}$, —NR$^{10}$R$^{11}$, —OC(O)R$^{10}$, —C(O)OR$^{10}$, —C(O)R$^{10}$, —OC(O)OR$^{10}$, —C(O)NR$^{10}$R$^{11}$, —OC(O)NR$^{10}$R$^{11}$, —NR$^{10}$C(O)R$^{11}$, —NR$^{10}$C(O)OR$^{11}$ and —NR$^{10}$C(O)NR$^{11}$. In other aspects of these embodiments, R$^9$ is —CH═CH$_2$. In other aspects of these embodiments, R$^9$ is —NCO.

In other embodiments, R$^2$ is C$_2$-C$_8$ alkenyl, wherein each hydrogen atom in R$^2$ is independently optionally substituted by an R$^3$. In some aspects of these embodiments, R$^3$ is halo.

In some embodiments, the long chain fluorinated alkyl is 8/2, 6/2 or 4/2.

In some embodiments, the long chain fluorinated alkyl is 6/2, and R$^2$ is C$_1$-C$_8$ alkyl. In some embodiments, the long chain fluorinated alkyl is 6/2, and R$^2$ is C$_1$-C$_8$ alkyl. In some embodiments, the long chain fluorinated alkyl is 6/2, and R$^2$ is propyl. In some embodiments, the long chain fluorinated alkyl is 6/2, and R$^2$ is C$_1$-C$_8$ alkyl, substituted by one —OC(O)R$^4$. In some embodiments, the long chain fluorinated alkyl is 6/2, and R$^2$ is C$_1$-C$_8$ alkyl, substituted by one R$^3$ that is —OC(O)R$^4$, and R$^4$ is C$_1$-C$_8$ alkyl. In some embodiments, the long chain fluorinated alkyl is 6/2, and R$^2$ is propyl acetate.

In another embodiment, the disclosure provides an article comprising a synthetic blend copolymer as described herein. In some aspects of these embodiments, the synthetic blend copolymer is made from polymerization of a compound as described herein bearing at least one polymerizable group, such as an acrylate, with at least one suitable monomer. In some aspects of these embodiments, the suitable monomer is an acrylate monomer, such as a methacrylate or a methylmethacrylate.

In another embodiment, the disclosure provides an article comprising one or more compounds of the formula

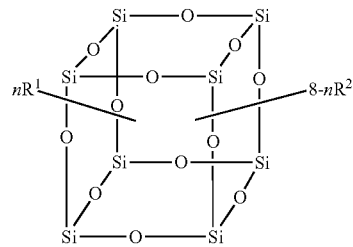

wherein n, R$^1$ and R$^2$ are as defined herein. In some aspects of these embodiments, the compound used in the article can that of any of the embodiments described above.

In another embodiment, the disclosure provides an article comprising one or more compounds of the formula

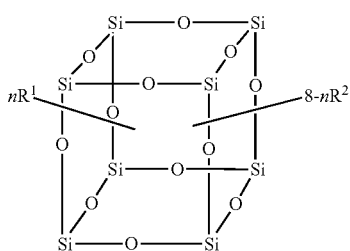

wherein n, $R^1$ and $R^2$ are as defined herein, produced by the process as described herein. In some aspects of these embodiments, the compound used in the article can be that of any of the embodiments described above.

Other features will become apparent upon reading the following detailed description of certain exemplary embodiments, when taken in conjunction with the appended claims.

BRIEF DESCRIPTION OF THE DRAWINGS

The drawings disclose exemplary embodiments in which like reference characters designate the same or similar parts throughout the figures of which.

DEFINITIONS

Figure 1:
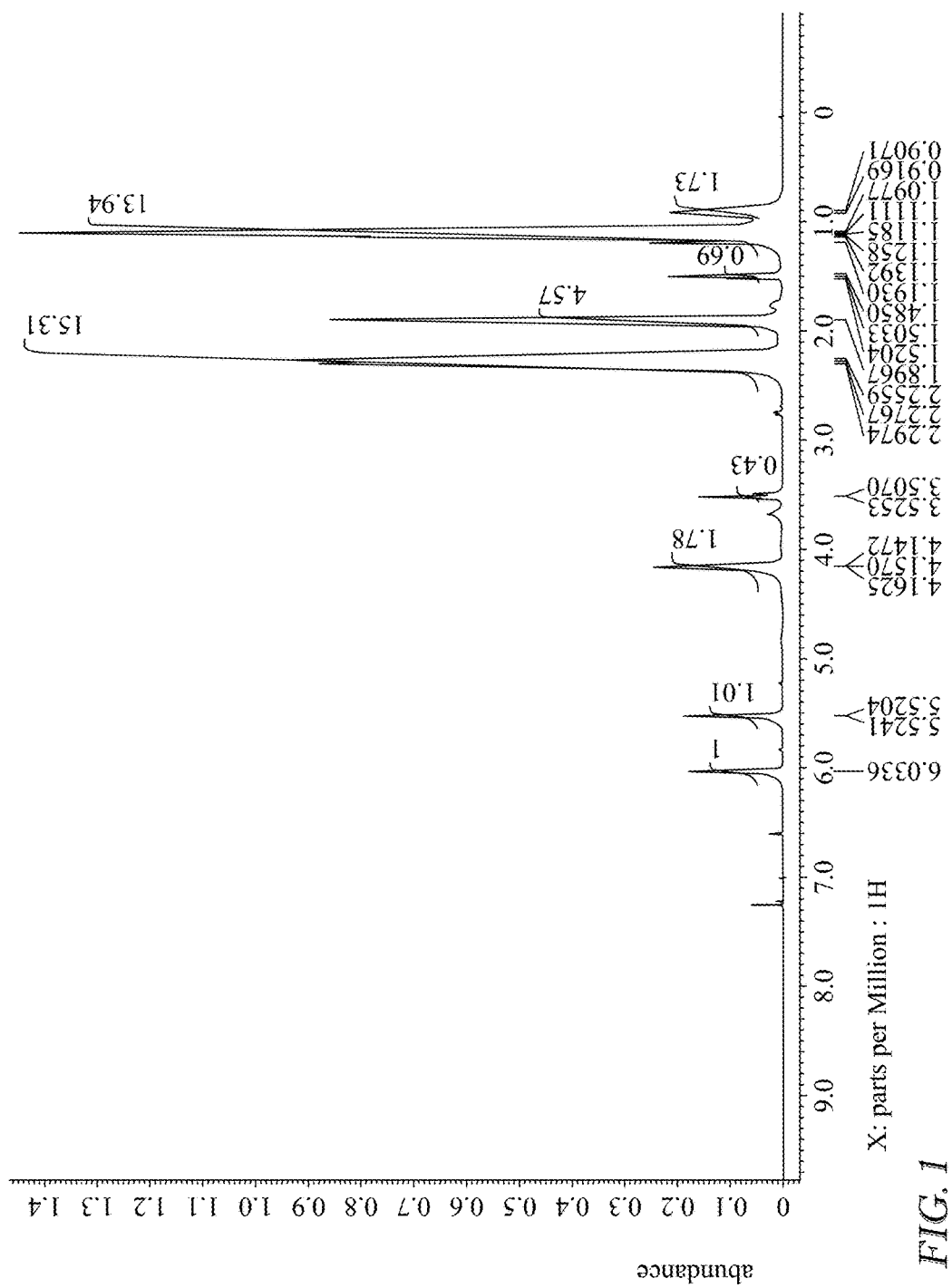
FIG. 1 is an analysis plot of $^1$H NMR analysis for synthetic blend of 4/2 Precursor (1H,1H,2H,2H-nonafluorohexyltriethoxysilane) and 3-methacryloxypropyl-triethoxysilane according to Example 1.

As used herein, the term "long-chain fluorinated alkyl" means any straight chain or branched chain alkyl group having from 5 to 12 carbon atoms in the longest continuous chain of carbon atoms as counted from the point of attachment of the chain of carbon atoms to the silicon atom at any apex of the silicon-oxide core, where at least one hydrogen atom in the straight chain or branched chain alkyl group is replaced by a fluorine atom. Any number of hydrogen atoms in the straight chain or branched chain alkyl group can be replaced with fluorine atoms within the meaning of "long-chain fluorinated alkyl" as used herein. For example, the terminal methyl group of a straight chain alkyl group having six carbon atoms in the chain (e.g. a hexyl group) can have each of the pendent hydrogen atoms replaced by a fluorine atom (e.g. a trifluoromethyl) to provide a long chain fluorinated alkyl group having the formula —$CH_2CH_2CH_2CH_2CH_2CF_3$. In another example, the last two carbon atoms of a straight chain alkyl group having six carbon atoms in the chain can have each of the pendent hydrogen atoms replaced by a fluorine atom (e.g. a trifluoroethyl) to provide a long chain fluorinated alkyl group having the formula —$CH_2CH_2CH_2CH_2CF_2CF_3$. This exemplary pattern can be continued to include within the definition of "long chain fluorinated alkyl" groups of the formula —$CH_2CH_2CH_2CF_2CF_2CF_3$, —$CH_2CH_2CF_2CF_2CF_2CF_3$, —$CH_2CF_2CF_2CF_2CF_2CF_3$, and —$CF_2CF_2CF_2CF_2CF_2CF_3$. As is commonly known in the art, an alkyl group where every hydrogen atoms in the chain is replaced by a fluorine atom is known as a "perfluorinated" alkyl group.

When less than all of the carbon atoms in the longest continuous chain of carbon atoms have hydrogens replaced by fluorine atoms, the "long chain fluorinated alkyl" group can be identified by the shorthand X/Y, where X is the number of terminal carbon atoms in the longest continuous chain of carbon atoms as counted from the point of attachment of the chain of carbon atoms to the silicon atom at any apex of the silicon-oxide core, and Y is the remaining number of carbon atoms in the longest continuous chain of carbon atoms on which hydrogen atoms are not replaced by fluorine atoms. For example, a long chain fluorinated alkyl group of the formula —$CH_2CH_2CF_2CF_2CF_2CF_3$ can be given the shorthand 4/2. Other exemplary long chain fluorinated alkyl groups include but are not limited to 3/3, 6/2, 4/4, 8/2, 6/4 and the like.

When the shorthand X/Y is used herein in connection with F-POSS, the name provided refers to the F-POSS molecule each of the groups attached to the apices of the silicon-oxide core is of the long chain fluorinated alkyl group type defined by the X/Y. For example, 6/2 F-POSS refers to an F-POSS molecule of Formula I, wherein each of the R groups at the apices of the silicon-oxide core is a 6/2 long chain fluorinated alkyl group as defined herein.

As used herein, "alkyl" refers to a saturated aliphatic hydrocarbon radical including straight chain and branched chain groups of 1 to 20 carbon atoms (e.g. $C_1$-$C_{20}$), preferably 1 to 12 carbon atoms (e.g. $C_1$-$C_{12}$), more preferably 1 to 8 carbon atoms (e.g. $C_1$-$C_8$), or 1 to 6 carbon atoms (e.g. $C_1$-$C_6$), or 1 to 4 carbon atoms (e.g. $C_1$-$C_4$). "Lower alkyl" refers specifically to an alkyl group with 1 to 4 carbon atoms. Examples of alkyl groups include methyl, ethyl, propyl, 2-propyl, n-butyl, iso-butyl, tert-butyl, pentyl, and the like. Alkyl may be substituted or unsubstituted. Typical substituent groups include those conventionally known in the art, such as cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^xR^y$, where $R^x$ and $R^y$ are independently selected from the group consisting of hydrogen, alkyl, cycloalkyl, aryl, carbonyl, acetyl, sulfonyl, trifluoromethanesulfonyl and, combined, a five- or six-member heteroalicyclic ring. Substituent groups also include those described elsewhere in this disclosure in connection with alkyl.

As used herein, "cycloaylkyl" refers to a 3 to 10 member all-carbon monocyclic ring ($C_3$-$C_{10}$), an all-carbon 5-member/6-member or 6-member/6-member fused bicyclic ring (a "fused" ring system means that each ring in the system shares an adjacent pair of carbon atoms with each other ring in the system) wherein one or more of the rings may contain one or more double bonds but none of the rings has a completely conjugated pi-electron system. "Cycloalkyl" includes 3 to 8 member all-carbon monocyclic ring (e.g. "$C_3$-$C_8$ cycloalkyl"), Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —NR$^x$R$^y$, with R$^x$ and R$^y$ as defined above. Substituent groups also include those described elsewhere in this disclosure in connection with cycloalkyl.

As used herein, "alkenyl" refers to an alkyl group, as defined herein, of at least two carbon atoms in length further defined by the inclusion of at least one carbon-carbon double bond ("C=C"). "Alkenyl" includes groups having from 2 to 8 carbon atoms and at least one carbon-carbon double bond (e.g. "C$_2$-C$_8$ alkenyl"). Representative examples include, but are not limited to, ethenyl, 1-propenyl, 2-propenyl, 1-, 2-, or 3-butenyl, and the like. Alkenyl may be substituted as described above for alkyl, or alkenyl may be unsubstituted. Substituent groups also include those described elsewhere in this disclosure in connection with alkenyl.

As used herein, "alkynyl" refers to an alkyl group, as defined herein, of at least two carbon atoms in length further defined by the inclusion of at least one carbon-carbon triple bond ("C≡C"). "Alkynyl" includes groups having from 2 to 8 carbon atoms and at least one carbon-carbon triple bond (e.g. "C$_2$-C$_8$ alkynyl"). Representative examples include, but are not limited to, ethynyl, 1-propynyl, 2-propynyl, 1-, 2-, or 3-butynyl, and the like. Alkynyl may be substituted as described above for alkyl, or alkynyl may be unsubstituted. Substituent groups also include those described elsewhere in this disclosure in connection with alkynyl.

As used herein, "aryl" refers to an all-carbon monocyclic or fused-ring polycyclic groups of 6 to 14 carbon atoms (C$_6$-C$_{14}$) having a completely conjugated pi-electron system. Aryl includes all-carbon monocyclic or fused-ring polycyclic groups of 6 to 10 carbon atoms (e.g., "C$_6$-C$_{10}$ aryl"). Examples, without limitation, of aryl groups are phenyl, naphthalenyl and anthracenyl. The aryl group may be substituted as described above for alkyl, or aryl may be unsubstituted. Substituent groups also include those described elsewhere in this disclosure in connection with aryl.

As used herein, "heteroaryl" refers to a monocyclic or fused ring group of 5 to 12 ring atoms containing one, two, three or four ring heteroatoms selected from N, O, and S, the remaining ring atoms being C, and, in addition, having a completely conjugated pi-electron system. "Heteroaryl" includes groups as defined herein having from five to seven ring atoms (e.g., "5-7 membered heteroaryl"). Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted as described above for alkyl, or heteroaryl may be unsubstituted. Substituent groups also include those described elsewhere in this disclosure in connection with heteroaryl.

As used herein. "heterocyclic" refers to a monocyclic or fused ring group having in the ring(s) of 3 to 12 ring atoms, in which one or two ring atoms are heteroatoms selected from N, O, and S(O)$_n$ (where n is 0, 1 or 2), the remaining ring atoms being C. The rings may also have one or more double bonds. However, the rings do not have a completely conjugated pi-electron system. "Heterocyclic" includes groups as defined herein having from five to seven ring atoms (e.g., "5-7 membered heterocyclic"). The heterocyclic group may be substituted as described above for alkyl, or heterocyclic may be unsubstituted. Substituent groups also include those described elsewhere in this disclosure in connection with heterocyclic.

As used herein, "alkoxy" refers to both an —O-(alkyl) or an —O-(cycloalkyl) group. "Alkoxy" includes groups having from 1 to 8 carbon atoms (e.g., "C$_1$-C$_8$ alkoxy"). The alkoxy group may be substituted as described above for alkyl or it can be unsubstituted. Substituent groups also include those described elsewhere in this disclosure in connection with alkoxy. Representative examples include, but are not limited to, methoxy, ethoxy, propoxy, cyclopropyloxy, cyclobutyloxy, cyclopentyloxy, cyclohexyloxy, and the like.

DETAILED DESCRIPTION

Silsesquioxanes have a cage-like structure, which is most commonly a cube, hexagonal prism, octagonal prism, decagonal prism, or dodecagonal prism. In exemplary embodiments, of the various possible F-POSS cage molecular structures, the cube-like ("T8") cage structure is provided in connection with the invention. F-POSS molecules consist of a silicon-oxide core [SiO$_{1.5}$] with a periphery of long-chain fluorinated alkyl groups.

In exemplary embodiments, the present disclosure provides F-POSS compositions made of a blend of feedstock materials. In one exemplary embodiment, a first feedstock comprises a long-chain fluorinated alkyl triethoxysilane and a second feedstock comprises a functionalized triethoxysilane, where the functionalized triethoxysilane can be of the formula R$^2$Si(OR$^A$)$_3$ where R$^2$ is as defined herein and R$^A$ is a C$_1$-C$_8$ alkoxy. The process for preparing compounds described in the disclosure can be represented by the following scheme.

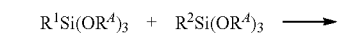

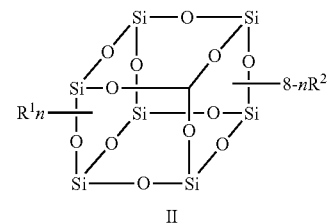

II where R$^1$, R$^2$ and n are as defined herein, and R$^A$ can be any alkoxy, for example C$_1$-C$_8$ alkoxy. It will be appreciated that the alkoxy can be the same or different on each of the reagents in the scheme above. In the present compositions, the blend of molecules may, in exemplary embodiments, form a Gaussian distribution of molecules having different ratios of R$^1$ and R$^2$. For example, in one exemplary embodiment, one portion of the blend may be made up of an F-POSS molecule with a molar ratio of R$^1$:R$^2$=8:0, in other words, all eight apices have R$^1$ (e.g., n=8). Another portion may have a molar ratio of R$^1$:R$^2$=7:1, in other words, seven of the apices have R$^1$ and one apex has R$^2$ (e.g., n=7). Another portion has a ratio of 6:2 (e.g., n=6). And, other portions have ratios of 5:3 (e.g., n=5), 4:4 (e.g., n=4), 3:5 (e.g., n=3), 2:6 (e.g., n=2), 1:7 (e.g., n=1) and 0:8 (e.g., n=0). In exemplary embodiments, the distribution of R1:R2 ratios generally comprises a Gaussian distribution. In exemplary embodiments, the distribution of ratios can be predetermined to an extent, or tuned, based on reaction conditions and amounts used of each substituent.

It will be further appreciated that the reaction present above is not limited to two feedstocks. For example, a reaction is contemplated where a first feedstock comprises a long-chain fluorinated alkyl triethoxysilane, a second feedstock comprises a second long-chain fluorinated alkyl triethoxysilane, and a third feedstock comprises a functionalized triethoxysilane. Alternatively, a reaction is contemplated where a first feedstock comprises a long-chain fluorinated alkyl triethoxysilane, a second feedstock comprises a first functionalized triethoxysilane, and a third feedstock comprises a second functionalized triethoxysilane.

EXAMPLES

The following examples are set forth for purposes of illustration only. Parts and percentages appearing in such examples are by weight unless otherwise stipulated.

Materials 1H,1H,2H,2H-nonafluorohexyltriethoxysilane was obtained from TCI America. 3-methacryloxypropyltriethoxysilane was obtained from Gelest Inc. Tetraethylammonium hydroxide in water was obtained from Acros Organics (Code 420291000, lot A0322694). Hexafluorobenzene was obtained from Aldrich (H8706-100G, lot MKBS2573V). Diethyl ether was obtained from Acros Organics (61508-5000, lot B0527523). 2,2'-Azobis(2-methylpropionitrile), 98%, was obtained from Sigma-Aldrich.

Example 1A: Synthetic Blend 4/2 F-POSS-Methacrylate (SB 4/2 F-POSS-MA) Monomer Synthesis—Synthetic Blend of 4/2 Precursor (1H,1H,2H,2H-nonafluorohexyltriethoxysilane) and 3-methacryloxypropyl-triethoxysilane 1.8 g of the 4/2 F-POSS precursor 1H,1H,2H,2H-nonafluorohexyltriethoxysilane (MW 410.35; 4.38 mmol) and 0.18 g of 3-methacryloxypropyltriethoxysilane (MW 290.43; 0.62 mmol) were taken in a 7:1 molar ratio. To this was added 5 mL of dry THF, followed by the addition of 0.0105 mL of 25% tetraethylammonium hydroxide solution in water. The reaction mixture was agitated for 5 days at room temperature on an orbital shaker then allowed to stand undisturbed for another 7 days at room temperature. The reaction mixture was then concentrated down on a rotary evaporator, the residue taken up in diethyl ether, followed by washing the organic layer with water and drying over anhydrous $MgSO_4$. The organic layer was concentrated down again and the residue dried under vacuum at 50° C. to provide 1.12 g of the desired SB 4/2 F-POSS-MA monomer as a gooey solid.

$^1$H NMR of the product was obtained by dissolving it in hexafluorobenzene with a few drops of chloroform-d as shown in FIG. 1.

Example 1B: Synthetic Blend 6/2 F-POSS-Propylacetate (SB 6/2 F-POSS-Propylacetate) Monomer Synthesis—Synthetic Blend of 6/2 Precursor (1H,1H,2H,2H-Tridecafluorooctyltriethoxysilane) and (3-Acetoxypropyl)trimethoxysilane A reaction vessel was charged with 15 g of 1H,1H,2H,2H-Tridecafluorooctyltriethoxysilane, (Gelest (SIT8175.0, CAS: 51851-37-7), 29.5 mmol, 7 eq), 0.935 g of 3-Acetoxypropyl)trimethoxysilane (Gelest (SIA0100.0, CAS: 599004-18-1), 4.2 mmol, 1 eq) was dissolved in 25 mL of a solution of Potassium Hydroxide (Sigma Aldrich, P1767, CAS 1310-58-3) in Water (DI or Store bought by the gal) and 15 mL of deionized water, followed by 2.5 mL of aqueous 2-Propanol (Alfa Aesar (36644, 99.5%, CAS 67-63-0), 10 mg/mL). The reaction was stirred for 3 days at room temperature. The precipitated solids were filtered to provide 9.84 g (79% yield) of the desired product.

Mp 121.5° C.; $^1$H NMR (AK-225, 500 MHz): δ 0.82 (t, 2H), 1.07-1.05 (m, 14H), 1.8 (m, 2H), 2.3-2.21 (m, 14H), 2.52 (s, 3H), 4.05 (t, 2H); $^{19}$F NMR ((CD$_3$)$_2$CO, 470 MHz): δ 82.9 (21F), −117.4 (14F), −123.6 (14F), −124.2 (14F), −124.5 (14F), −127.7 (14F); Anal. Calcd for $C_{61}H_{37}F_{91}O_{12}Si_8$: C, 24.86; H, 1.27; F, 58.65. Found: C, 24.41; H, 1.02; F, 60.55.

Example 1C: Synthetic Blend 6/2 F-POSS-Propylacetate (SB 6/2 F-POSS-Propylacetate) Monomer Synthesis—Synthetic Blend of 6/2 Precursor (1H,1H,2H,2H-Tridecafluorooctyltriethoxysilane) and (3-Acetoxypropyl)trimethoxysilane (Scale-Up)

To a 12 L 3NRBF equipped with an overhead stirrer, 2 glass stoppers, cork ring, and a secondary container is charged with stirring, 2.075 L of Potassium Hydroxide (Sigma Aldrich, P1767, CAS 1310-58-3), 1245 g (2.44 moles) of 1H,1H,2H,2H-Tridecafluorooctyltriethoxysilane, (Gelest (SIT8175.0, CAS: 51851-37-7), 29.5 mmol, 7 eq), 77.61 g (0.351 moles) of 3-Acetoxypropyl)trimethoxysilane (Gelest (SIA0100.0, CAS: 599004-18-1). The mixture was stirred for 10 minutes, at which time 210 mL (10 mg/ml) of aqueous 2-Propanol (Alfa Aesar (36644, 99.5%, CAS 67-63-0), followed by 1.245 L of toluene. The reaction mixture was stirred at ambient temperature for 48-72 hrs. The reaction was filtered, washed with deionized water, and dried in a vacuum oven to provide 901 g (87.1% yield) of the desired product.

Example 2: Synthesis of 4/2 F-POSS-MA Synthetic Blend MMA Copolymer

Four separate comparison polymerization reactions were run under the same conditions with varying amounts of SB 4/2 F-POSS-MA monomer. (0, 1, 5 and 10 weight percent).

Figure 2:
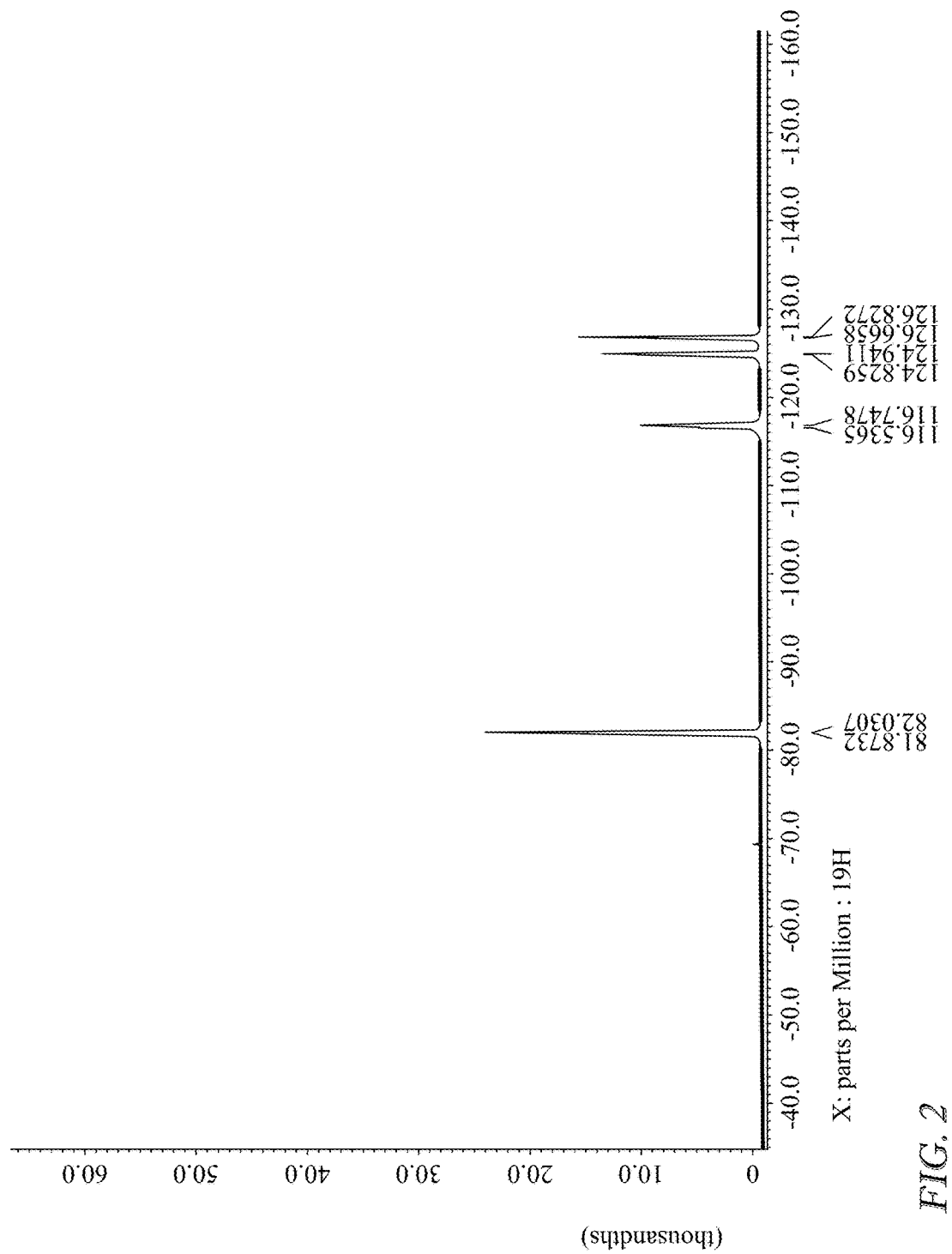
FIG. 2 is an analysis plot of $^{19}$F NMR analysis for 10% 4/2 FPOSS-MA synthetic blend MMA copolymer according to Example 2.

A reaction vessel was charged with 25 mL of 4:1 hexafluorobenzene/THF and degassed for 20 minutes. To the vessel was SB 4/2 F-POSS-MA monomer. (0, 1, 5 and 10 weight percent based on methylmethacrylate monomer), methyl methacrylate monomer (5 g total batch size), and 20 mg of 2,2'-azobis(2-methylpropionitrile) initiator. The reaction was run under nitrogen for 18 hours at 70° C. The reaction solution was poured into 150 mL of hexane and stirred with a spatula to break up the clumps. The solid material was filtered, washed thoroughly with hexane, and dried under high vacuum at 45° C. overnight. Polymer yields are shown in Table 1. Each polymer was determined to be soluble in Acetone, Methyl ethyl ketone, Tetrahydrofuran, Acetonitrile. The polymers were not soluble in Isopropanol. $^{19}$F NMR was performed on the 10% 4/2 FPOSS-MA Synthetic Blend MMA copolymer. The NMR shows the incorporation of fluorine into the copolymer (See FIG. 2).

Polymer Yields:

TABLE 1

| Reaction | Yield |
|---|---|
| 0% SB 4/2 F-POSS-MA monomer | 2.38 g |
| 1% SB 4/2 F-POSS-MA monomer | 3.11 g |
| 5% SB 4/2 F-POSS-MA monomer | 2.18 g |
| 10% SB 4/2 F-POSS-MA monomer | 2.37 g |

Figure 3:
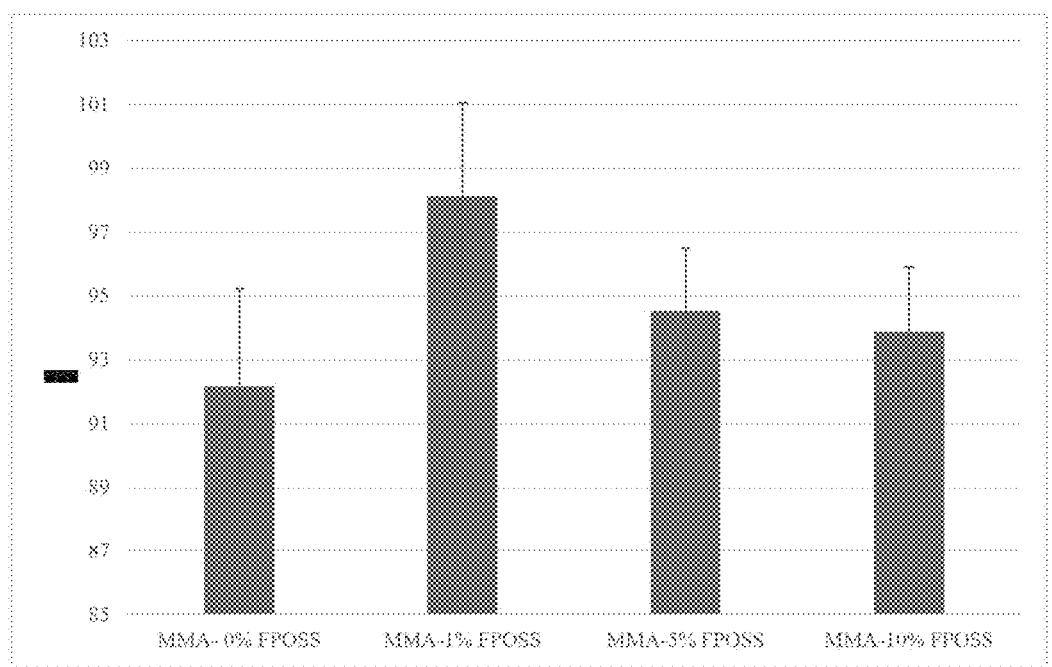
FIG. 3 is a graph of experiments showing the contact angle of water on 4/2 FPOSS-MA synthetic blend MMA copolymer (8% solids) on glass according to Example 3.
Figure 4:
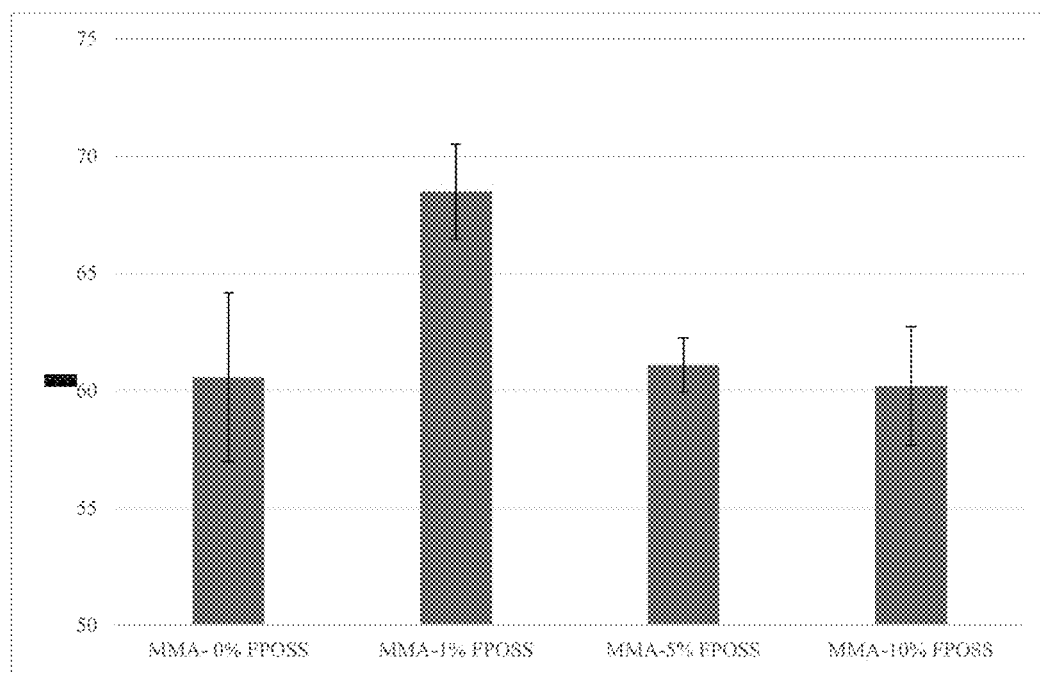
FIG. 4 is a graph of experiments showing the contact angle of hexadecane on 4/2 FPOSS-MA synthetic blend MMA copolymer (8% solids) on glass according to Example 3.

Example 3: 4/2 F-POSS-MA Synthetic Blend MMA Copolymer Contact Angle Measurements 50 mg of each polymer were dissolved in 600 μL of MEK (83.3 mg/mL). Each of the 4/2 FPOSS-MA Synthetic Blend MMA copolymers dissolved completely to a clear solution. The polymer solutions were then coated on microscope slides by blade coating (~50μ wet film thickness). Each FPOSS containing copolymer coated to a milky film. The coatings were dried overnight. Contact angle measurements of water and hexadecane were taken using a Kruss DSA100 drop shape analyzer (See FIGS. 3 and 4).

The following numbered clauses include embodiments that are contemplated and non-limiting:

Although only a number of exemplary embodiments have been described in detail above, those skilled in the art will readily appreciate that many modifications are possible in the exemplary embodiments without materially departing from the novel teachings and advantages. Accordingly, all such modifications are intended to be included within the scope of this disclosure as defined in the following Claims.

While the methods, equipment and systems have been described in connection with specific embodiments, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method Claim does not actually recite an order to be followed by its steps or it is not otherwise specifically stated in the Claims or descriptions that the steps are to be limited to a specific order, it is no way intended that an order be inferred, in any respect.

As used in the specification and the appended Claims, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and Claims of this specification, the word "comprise" and variations of the word, such as "comprising" and "comprises," means "including but not limited to," and is not intended to exclude, for example, other additives, components, integers or steps. The word "exemplary" or "illustrative" means "an example of" and is not intended to convey an indication of a preferred or ideal embodiment. "Such as" is not used in a restrictive sense, but for explanatory purposes.

Disclosed are components that can be used to perform the disclosed methods, equipment and systems. These and other components are disclosed herein, and it is understood that when combinations, subsets, interactions, groups, etc., of these components are disclosed that while specific reference of each various individual and collective combinations and permutation of these may not be explicitly disclosed, each is specifically contemplated and described herein, for all methods, equipment and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

It should further be noted that any patents, applications and publications referred to herein are incorporated by reference in their entirety.

The invention claimed is:

1. A process for preparing a compound having a formula

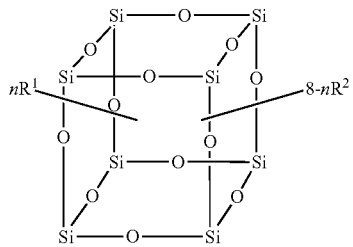

wherein, $R^1$ is a long chain fluorinated alkyl;

$R^2$ is selected from the group consisting of $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic and 5-7 membered heteroaryl, wherein each hydrogen atom in $R^2$ is independently optionally substituted by an $R^3$;

each $R^3$ is independently selected from the group consisting of halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —OR$^4$, —NR$^4$R$^5$, —OC(O)R$^4$, —C(O)OR$^4$, —C(O)R$^4$, —OC(O)OR$^4$, —C(O)NR$^4$R$^5$, —OC(O)NR$^4$R$^5$, —NR$^4$C(O)R$^5$, —NR$^4$C(O)OR$^5$ and —NR$^4$C(O)NR$^4$R$^5$, and when $R^3$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic or 5-7 membered heteroaryl, each hydrogen atom in $R^3$ is independently optionally substituted by an $R^6$;

each $R^4$ and $R^5$ is independently selected from the group consisting of hydrogen, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, and 5-7 membered heteroaryl, wherein each hydrogen atom in $R^4$ and $R^5$ is independently optionally substituted by an $R^6$;

each $R^6$ is independently selected from the group consisting of halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —OR$^7$, —NR$^7$R$^8$, —OC(O)R$^7$, —C(O)OR$^7$, —C(O)R$^7$, —OC(O)OR$^7$, —C(O)NR$^7$R$^8$, —OC(O)NR$^7$R$^8$, —NR$^7$C(O)R$^8$, —NR$^7$C(O)OR$^8$ and NR$^7$C(O)NR$^7$R$^8$, and when $R^6$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic or 5-7 membered heteroaryl, each hydrogen atom in $R^6$ is independently optionally substituted by an $R^9$;

each $R^7$ and $R^8$ is independently selected from the group consisting of hydrogen, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic and 5-7 membered heteroaryl, wherein each hydrogen atom in $R^7$ and $R^8$ is independently optionally substituted by one or more $R^9$;

each $R^9$ is independently selected from the group consisting of hydrogen, halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —OR$^{10}$, —NR$^{10}$R$^{11}$, —OC(O)R$^{10}$, —C(O)OR$^{10}$, —C(O)R$^{10}$, —OC(O)OR$^{10}$, —C(O)NR$^{10}$R$^{11}$, —OC(O)NR$^{10}$R$^{11}$, —NR$^{10}$C(O)R$^{11}$, —NR$^{10}$C(O)OR$^{11}$ and —NR$^{10}$C(O)NR$^{10}$R$^{11}$, and when R$^9$ is C$_1$-C$_8$ alkyl, C$_2$-C$_8$ alkenyl, C$_2$-C$_8$ alkynyl, C$_6$-C$_{10}$ aryl, C$_3$-C$_8$ cycloalkyl, 5-7 membered heterocyclic, C$_3$-C$_8$ cycloalkyl or 5-7 membered heteroaryl, each hydrogen in R$^9$ is independently optionally substituted by a moiety selected from the group consisting of halo, —NCO, —OR$^{10}$, —NR$^{10}$R$^{11}$, —OC(O)R$^{10}$, —C(O)OR$^{10}$, —C(O)R$^{10}$, —OC(O)OR$^{10}$, —C(O)NR$^{10}$R$^{11}$, —OC(O)NR$^{10}$R$^{11}$, —NR$^{10}$C(O)R$^{11}$, —NR$^{10}$C(O)OR$^{11}$ and —NR$^{10}$C(O)NR$^{10}$R$^{11}$;

each R$^{10}$ and R$^{11}$ is independently selected from the group consisting of H, C$_1$-C$_8$ alkyl, C$_2$-C$_8$ alkenyl and C$_2$-C$_8$ alkynyl, and when R$^{10}$ or R$^{11}$ are C$_1$-C$_8$ alkyl, C$_2$-C$_8$ alkenyl or C$_2$-C$_8$ alkynyl, each hydrogen atom in R$^{10}$ and R$^{11}$ is independently optionally substituted by a fluorine atom;

n is an integer from 1 to 7; and, each R$^1$ and R$^2$ is independently covalently attached at a silicon atom, comprising:

(a) contacting a compound of the formula R$^1$Si(OR$^4$)$_3$ with a compound of the formula R$^2$Si(OR$^4$)$_3$, in the presence of a base, wherein R$^4$ is a C$_1$-C$_8$ alkoxy, and the R$^4$ on R$^1$Si(OR$^4$)$_3$ and R$^2$Si(OR$^4$)$_3$ can be the same or different.

2. The process of claim 1, wherein R$^2$ is C$_1$-C$_8$ alkyl, wherein each hydrogen atom in R$^2$ is independently optionally substituted by an R$^3$.

3. The process of claim 1, wherein R$^3$ is —NCO, —OR$^4$, —OC(O)R$^4$, —C(O)OR$^4$, —C(O)R$^4$ or —OC(O)OR$^4$.

4. The process of claim 1, wherein R$^4$ is C$_1$-C$_8$ alkyl and wherein each hydrogen atom in R$^4$ is independently optionally substituted by an R$^6$.

5. The process of claim 1, wherein R$^4$ is C$_2$-C$_8$ alkenyl, wherein each hydrogen atom in R$^4$ is independently optionally substituted by an R$^6$.

6. The process of claim 1, wherein R$^6$ is C$_1$-C$_8$ alkyl, —NCO, —OR$^7$, —NR$^7$R$^8$, —OC(O)R$^7$, —C(O)OR$^7$, —C(O)R$^7$ or —OC(O)OR$^7$.

7. The process of claim 1, wherein R$^7$ is C$_1$-C$_8$ alkyl, C$_2$-C$_8$ alkenyl, C$_2$-C$_8$ alkynyl, C$_6$-C$_{10}$ aryl or 5-7 membered heteroaryl, wherein each hydrogen atom in R$^7$ is independently optionally substituted by one or more R$^9$.

8. The process of claim 1, wherein R$^9$ is hydrogen or C$_1$-C$_8$ alkyl, and when R$^9$ is C$_1$-C$_8$ alkyl, R$^9$ is optionally substituted by a —OC(O)R$^{10}$.

9. The process of claim 1, wherein R$^{10}$ is H or C$_1$-C$_8$ alkyl, and when R$^{10}$ is C$_1$-C$_8$ alkyl, each hydrogen atom in R$^{10}$ is independently optionally substituted by a fluorine atom.

10. The process of claim 1, wherein R$^2$ is n-propyl, wherein each hydrogen atom in R$^2$ is independently optionally substituted by an R$^3$.

11. The process of claim 10, wherein R$^3$ is —OC(O)R$^4$ or —OC(O)OR$^4$.

12. The process of claim 11, wherein R$^4$ is methyl.

13. The process of claim 11, wherein R$^4$ is —CH═CH$_2$, wherein each hydrogen atom in R$^4$ is independently optionally substituted by an R$^6$.

14. The process of claim 13, wherein R$^6$ is C$_1$-C$_8$ alkyl.

15. The process of claim 14, wherein R$^6$ is methyl.

16. The process of claim 10, wherein the long chain fluorinated alkyl is 8/2, 6/2 or 4/2.

17. The process of claim 1, wherein the long chain fluorinated alkyl is 8/2, 6/2 or 4/2.

18. The process of claim 1, wherein the base is potassium hydroxide or tetraethylammonium hydroxide.

19. The process of claim 2, wherein R$^3$ is —NH$_2$.

20. The process of claim 19, wherein the base is potassium hydroxide or tetraethylammonium hydroxide.

* * * * *